(12) United States Patent
Fitz

(10) Patent No.: US 8,133,233 B2
(45) Date of Patent: Mar. 13, 2012

(54) BONE PROTECTOR, KIT AND METHOD

(75) Inventor: Wolfgang Fitz, S. Natick, MA (US)

(73) Assignee: Depuy Products, Inc., Warsaw, IN (US)

( * ) Notice: Subject to any disclaimer, the term of this patent is extended or adjusted under 35 U.S.C. 154(b) by 159 days.

(21) Appl. No.: 12/641,356

(22) Filed: Dec. 18, 2009

(65) Prior Publication Data

US 2010/0125338 A1    May 20, 2010

Related U.S. Application Data

(62) Division of application No. 11/039,978, filed on Jan. 21, 2005, now Pat. No. 7,749,276.

(51) Int. Cl.
*A61B 17/58* (2006.01)
(52) U.S. Cl. .......................................................... 606/90
(58) Field of Classification Search ............... 623/14.12, 623/16.11, 20.14, 20.18–20.21
See application file for complete search history.

(56) References Cited

U.S. PATENT DOCUMENTS

| | | | |
|---|---|---|---|
| 3,806,961 A | 4/1974 | Muller | |
| 3,878,566 A | 4/1975 | Bechtol | |
| 3,927,423 A | 12/1975 | Swanson | |
| 3,964,106 A | 6/1976 | Hutter, Jr. | |
| 4,207,627 A | 6/1980 | Cloutier | |
| 4,240,162 A | 12/1980 | Devas | |
| 4,285,070 A | 8/1981 | Averill | |
| 4,888,021 A | 12/1989 | Forte | |
| 4,944,756 A | 7/1990 | Kenna | |
| 4,979,957 A | 12/1990 | Hodorek | |
| 5,181,924 A | 1/1993 | Gschwend | |
| 5,236,462 A | 8/1993 | Mikhail | |
| 5,326,361 A | 7/1994 | Hollister | |
| 5,383,937 A | 1/1995 | Mikhail | |
| 5,470,354 A * | 11/1995 | Hershberger et al. | ......... 128/898 |
| 5,480,443 A | 1/1996 | Elias | |
| 5,593,450 A | 1/1997 | Scott et al. | |
| 5,702,465 A | 12/1997 | Burkinshaw | |

(Continued)

FOREIGN PATENT DOCUMENTS

FR        2699068 A        6/1994

(Continued)

OTHER PUBLICATIONS

Japanese Search Report for Corresponding Application No. 2005-014537, dated Oct. 16, 2009, 3 Pages.

(Continued)

*Primary Examiner* — David Isabella
*Assistant Examiner* — Ann Schillinger

(57) ABSTRACT

A surgical kit includes an orthopaedic implant, an orthopaedic trial and a bone protector. All three components have bone-contacting surfaces sized and shaped to be placed against a resected bone surface. The orthopaedic implant and trial are thicker than the bone protector. The bone protector has a flat bearing surface while the implant and trial have curved articulating surfaces. In use, the bone protector is temporarily mounted on the resected bone surface to cover and protect the resected bone surface while other bones of the joint are resected. A retractor can be placed against the bone protector and used as a lever to move other bones of the joint for greater access during surgery. The bone protector serves as the fulcrum of the lever and protects the resected bone from damage. The kit, bone protector and method should be useful in minimally invasive total joint arthroplasty.

6 Claims, 9 Drawing Sheets

U.S. PATENT DOCUMENTS

| | | | |
|---|---|---|---|
| 5,702,467 | A | 12/1997 | Gabriel |
| 5,871,540 | A | 2/1999 | Weissman |
| 6,296,646 | B1 | 10/2001 | Williamson |
| 6,478,799 | B1 | 11/2002 | Williamson |
| 6,589,248 | B1 | 7/2003 | Hughes |
| 6,616,696 | B1 | 9/2003 | Merchant |
| 6,709,460 | B2 | 3/2004 | Merchant |
| 2002/0029045 | A1* | 3/2002 | Bonutti ............... 606/86 |
| 2002/0290045 | | 3/2002 | Bonutti |
| 2002/0133164 | A1 | 9/2002 | Williamson |

FOREIGN PATENT DOCUMENTS

| | | | |
|---|---|---|---|
| FR | 2737848 | A | 2/1997 |

OTHER PUBLICATIONS

Australian Search Report Dated Sep. 7, 2009 in Co-Pending Australian Patent Application No. 2005200104.

European Search Report Dated Apr. 25, 2005 for Co-Pending European Application No. 05250109.5.

Papagelopoulos, Panayiotis J., Sim, Franklin H. and Morrey, Bernard F., "Patellectomy and Reconstructive Surgery for Disorders of the Patellofemoral Joint," Reconstructive Surgery of the Joints, 2d edition 1996, edited by Bernard F. Morrey, M.D., Churchil Livingston, New York, NY, vol. 2, ch. 121, pp. 1671-1699.

Insall, John M., "Historical Development, Classification and Characteristics of Knee Prostheses," Surgery of the Knee, 2d ed. 1993, edited by John N. Insall, M.D., Churchill Livingston, New York, NY, ch. 23, pp. 677, 707-711.

Tooms, Robert E., "Arthroplasty of Ankle and Knee," Campbell's Operative Orthopaedics, M.D., $8^{th}$ ed. 1992, edited by A.H. Crenshaw, Mosby, New York, NY, vol. 1, ch. 15, pp. 389, 411-412.

Rosenberg, Aaron G., "Surgical Technique of Posterior Cruciate Sacrificing, and Preserving Total Knee Arthroplasty," Total Knee Arthroplasty, 1993, edited by James A. Rand, M.D., Raven Press, Ltd., New York, NY 1993.

DePuy Orthopaedics, Inc., "LCS® PFJ Prosthesis, a Modular Patellofemoral Joint Replacement," Surgical Technique, 2004, DePuy Orthopaedics, Inc., Warsaw, IN.

DePuy Orthopaedics, Inc., "P.F.C. Σ Patella Planing System," Reference Guide and Surgical Technique, 2000, DePuy Orthopaedics, Inc., Warsaw, IN.

* cited by examiner

BONE PROTECTOR, KIT AND METHOD

CROSS-REFERENCE TO RELATED APPLICATIONS

This is a divisional patent application of and claims priority to U.S. patent Ser. No. 11/039978 of the same title and filed on Jan. 21, 2005.

This application claims priority to U.S. Provisional Application Ser. No. 60/538,661 filed on Jan. 23, 2004 by Wolfgang Fitz, entitled "Bone Protector, Kit & Method," which is incorporated by reference herein in its entirety.

FIELD OF THE INVENTION

This invention relates generally to a surgical technique for total joint replacement with minimal trauma to tissue and to a device and surgical kit to be used in minimizing trauma to tissue.

BACKGROUND OF THE INVENTION

Total knee replacement (TKR) surgery and component systems for replacing compartments of a knee in total replacement surgery are well known. The long-term goals of TKR are to help relieve pain, improve joint function and provide a durable reconstruction with proper component and limb alignment. Typically, the surgery involves resecting the distal end of a femur so a prosthetic femoral implant component may be mounted to the femur. The prosthetic femoral implant component replaces the lateral condyle, medial condyle, and patellofemoral portions of the femur because one or more of these areas of the knee are diseased.

In TKR surgery, the proximal end of the tibia is also resected so that a prosthetic tibial implant component may be mounted to the tibia to receive the lateral and medial condyles of the femoral component. The prosthetic tibial implant component may be comprised of a material having a low coefficient of friction to simulate the meniscus being replaced by the tibial component. Commonly, the prosthetic tibial implant component is two-piece, comprising a tibial tray to be mounted to the tibia and a low-friction bearing insert to be mounted to the tibial tray and to receive the condyles of the femoral implant component.

In TKR surgery, a portion of the patella is also resected so that a prosthetic patellar implant component may be mounted to the patella. The prosthetic patellar implant component typically includes a material with a low coefficient of friction that moves along a portion of the prosthetic femoral implant component as the patient flexes and extends the leg. In some prosthetic patellar implant components, the entire implant is made of a low-friction material; in others, a low-friction bearing is mounted to a metal base.

The mechanical properties of the resected patella are inferior. The force of a retractor pushing against the resected surface can be substantial, and may lead to damage or even fracture of the thin patella. In addition, some TKR patients are older and may have substantial inferior bone quality due to osteopenia. Therefore the resected patella is also susceptible to additional damage, for example, by a saw blade. The problems associated with the inferior mechanical properties of the resected patella are avoided in TKR procedures by performing the patellar resection after the femoral and tibial resections.

However, the patella and its associated soft tissues cover substantial parts of the distal femur and proximal tibia. Accordingly, to expose the distal femur and proximal tibia, the patella is first everted laterally to expose the distal femur and proximal tibia. In everting the patella, it is turned inside out, about 180 degrees. The distal femur and proximal tibia are resected and prepared to receive the prosthetic femoral and tibial components. The patella is then resected after the femur and tibia have been resected.

Because the patella is everted, or turned inside out, during TKR, the soft tissue envelope of the knee is disrupted and the soft tissue can be placed under substantial stress. The stress on this soft tissue can disrupt the quadriceps mechanism and traumatize the extensor mechanism of the knee. This stress and trauma can lead to post-operative pain and discomfort, and the time required for patient recovery can be extensive. In addition, violation of the suprapatellar pouch can lead to heterotopic ossification and arthrofibrosis.

Accordingly, there is a need for a system and method for performing TKR surgery that achieves the long-term goals discussed above, but that also achieves the following short-term goals: minimize soft tissue trauma, minimize surgical morbidity and help speed patient recovery.

SUMMARY OF THE INVENTION

The need for a system and method for performing TKR surgery with minimal disruption of the soft tissue envelope of the knee is met by the surgical method, surgical kit and bone protector of the present invention.

In one aspect, the present invention provides a surgical method of performing total knee arthroplasty. The method comprises resecting and covering a portion of the patella before resecting a portion of the distal femur and proximal tibia. In this method, the patella is subluxated rather than everted, so soft tissue trauma is minimized In addition, the resected patella is protected from damage from the subluxation.

In another aspect, the present invention provides a bone protector that can be used in the surgical method to cover and protect the resected patella. The bone protector comprises a bone-contacting surface and an opposite bearing surface. A mounting member is provided on the bone-contacting surface for temporarily mounting the bone protector to a surface of a bone. The bone protector has a thickness between the bone-contacting surface and the bearing surface. The bearing surface is substantially flat.

In another aspect, the present invention provides a surgical kit for prosthetic implants for replacing portions of bones of a joint. The kit comprises a first prosthetic implant component, a first prosthetic trial component and a bone protector. The first prosthetic implant component has a bone-contacting surface and an articulating surface. The first prosthetic trial component also has a bone-contacting surface and an articulating surface. The bone protector has a bone-contacting surface and a bearing surface. The first prosthetic implant component, first prosthetic trial component and bone protector are all capable of being separately mounted to a portion of the same bone. The bearing surface of the bone protector has a different shape than the articulating surfaces of the prosthetic implant component and prosthetic trial component.

In another aspect, the present invention provides a surgical kit for prosthetic implants for replacing portions of bones of a joint. The kit comprises a first prosthetic implant component, a first prosthetic trial component and a bone protector. The first prosthetic implant component has a bone-contacting surface, an articulating surface, and a thickness between the bone-contacting surface and the articulating surface. The first prosthetic trial component has a bone-contacting surface, an articulating surface, and a thickness between the bone-contacting surface and the articulating surface. The bone protector has a bone-contacting surface, a bearing surface, and a thickness between the bone-contacting surface and the bearing surface. The first prosthetic implant component, first prosthetic trial component and bone protector are all capable of being separately mounted to a portion of the same bone. The thickness of the bone protector is less than the thickness of the first prosthetic implant component and less than the thickness of the first prosthetic trial component.

DETAILED DESCRIPTION OF THE ILLUSTRATED EMBODIMENT

Bone protectors and a prosthetic implant system incorporating the principles of the present invention are illustrated in the accompanying drawings. The first illustrated bone protector is a patella protector. The principles of the present invention can also be applied to other bones, such as the femur and tibia, and embodiments of bone protectors for use in TKR are also illustrated in the accompanying drawings. It should be understood that the principles of the present invention can be applied to the replacement of the bones of other joints as well, and that the invention is not limited to any particular bone unless expressly set forth in the claims.

As described in more detail below, the present invention also provides a surgical technique. While this technique may be used to advantage with the bone protectors of the present invention, the invention is not limited to any particular surgical technique unless expressly set forth in the claims.

FIGS. 1-4 illustrate a patella protector 10. The illustrated patella protector comprises a thin wafer, with a bearing surface 12 and a bone-contacting surface 14. The first illustrated patella protector 10 also includes a plurality of mounting members 16, 18, 20. In the illustrated embodiment, each mounting member comprises a peg that is sized and shaped to be received in a mating hole formed in the resected surface of the patella. It should be understood that fewer or more mounting members could be provided; for example, the patella protector could have a single mounting member. In addition, although the mounting members comprise pegs in the illustrated embodiment, the invention is not limited to use of such pegs unless expressly set forth in the claims.

The patella protector 10 is generally provided as part of a system or surgical kit that would also include a patellar implant and a patellar trial. Generally, several sizes of the implant components and trials would be provided to accommodate the needs of the individual patient. Similarly, the system or surgical kit could also include several sizes of patella protectors as well. Typically, a patella protector corresponding in size and shape to each size and shape of implant and trial would be included in the kit.

Figure 1:
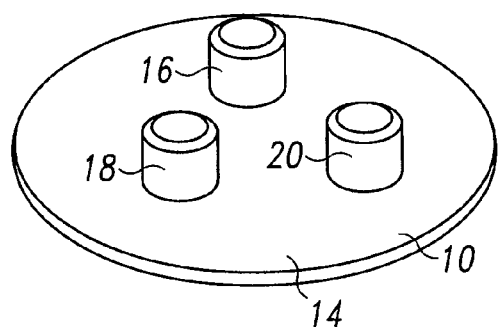
FIG. 1 is perspective view of a patella protector incorporating the principles of the present invention, showing the bone-contacting surface and mounting members of the patella protector.
Figure 2:
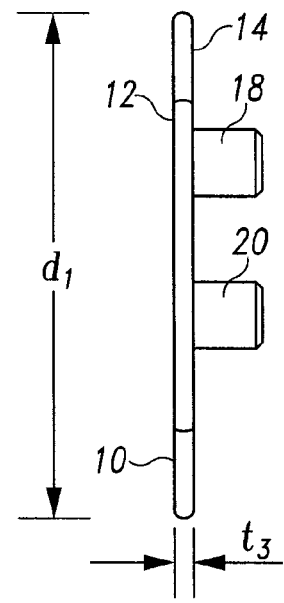
FIG. 2 is a side elevation of the patella protector of FIG. 1.
Figure 3:
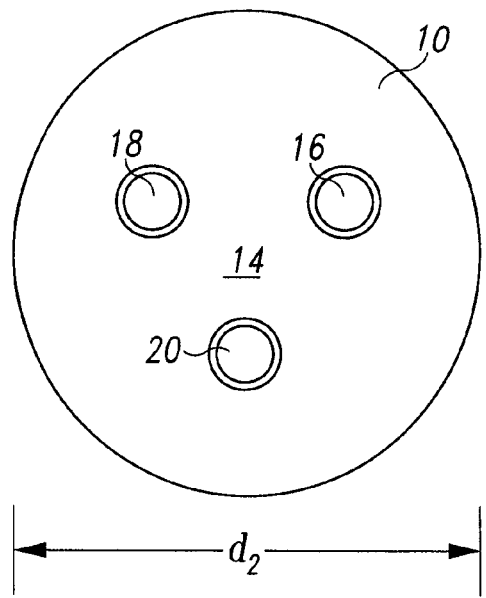
FIG. 3 is a bottom plan view of the patella protector of FIGS. 1-2.
Figure 4:
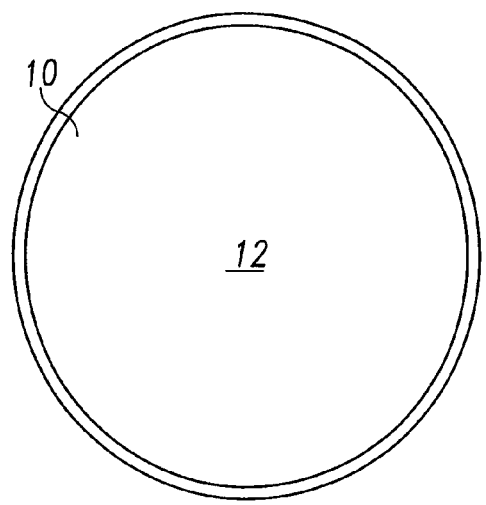
FIG. 4 is a top plan view of the patella protector of FIG. 13.
Figure 5:
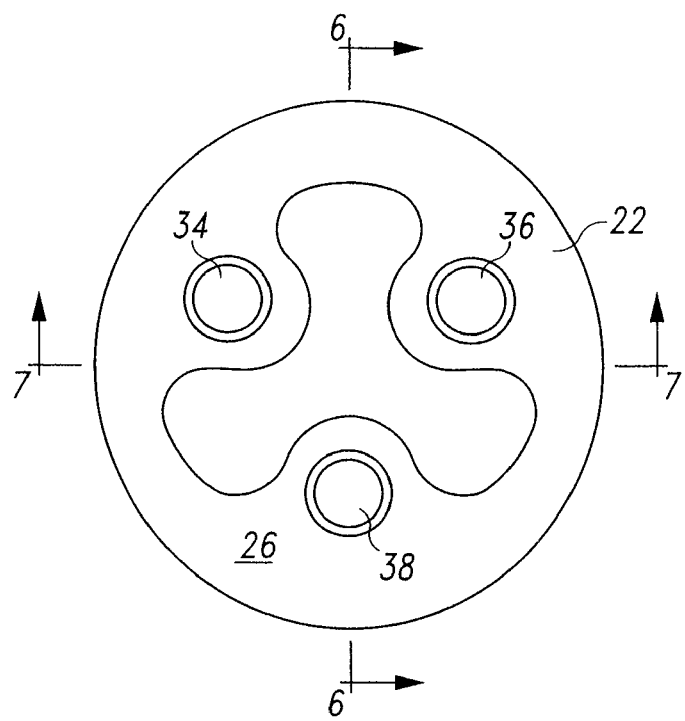
FIG. 5 is a bottom plan view of a prosthetic patellar implant that can be used with the patella protector of FIGS. 1-4.
Figure 6:
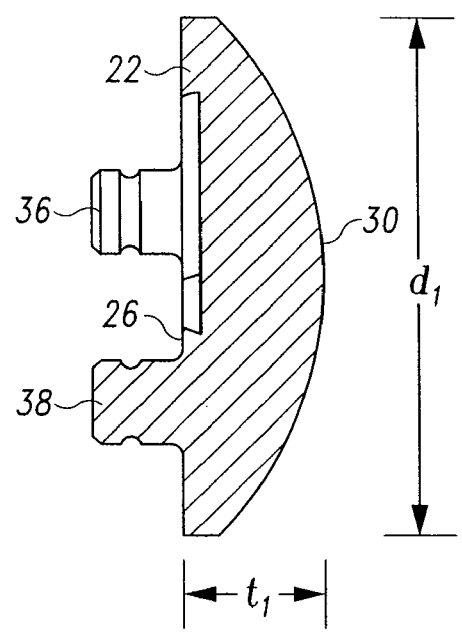
FIG. 6 is a cross-section of the prosthetic patellar implant of FIG. 5, taken along line 6-6 of FIG. 5.
Figure 7:
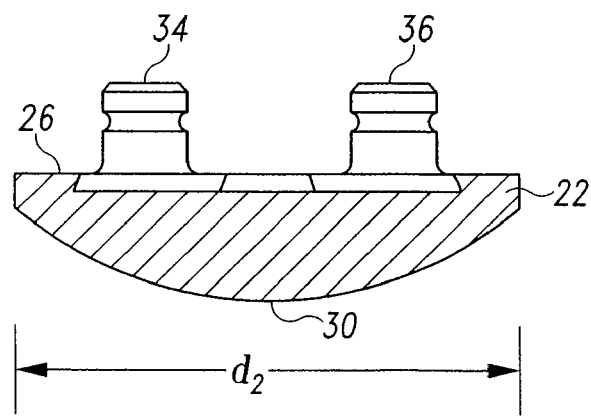
FIG. 7 is a cross-section of the prosthetic patellar implant of FIG. 5, taken along line 7-7 of FIG. 5.
Figure 8:
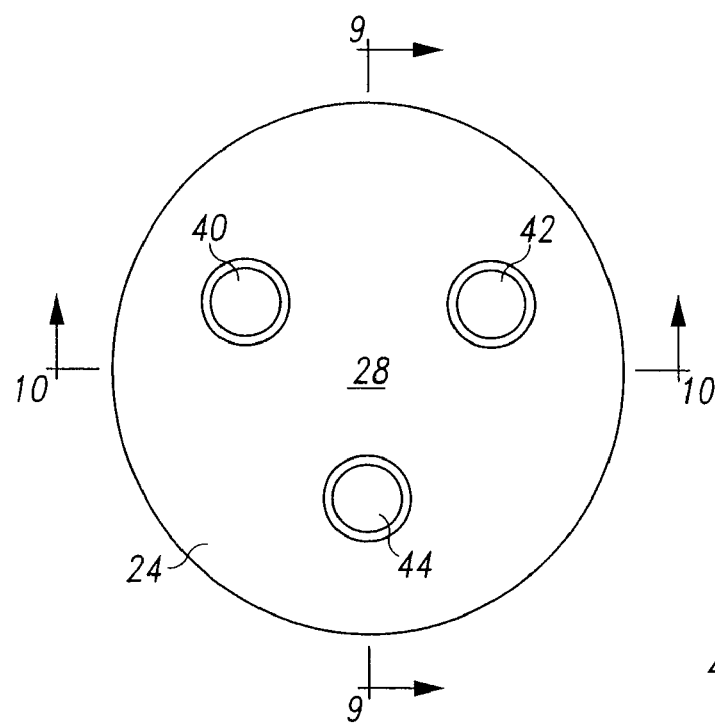
FIG. 8 is a bottom plan view of a patellar trial that can be used with the patella protector of FIGS. 1-4 and implant of FIGS. 5-8.
Figure 9:
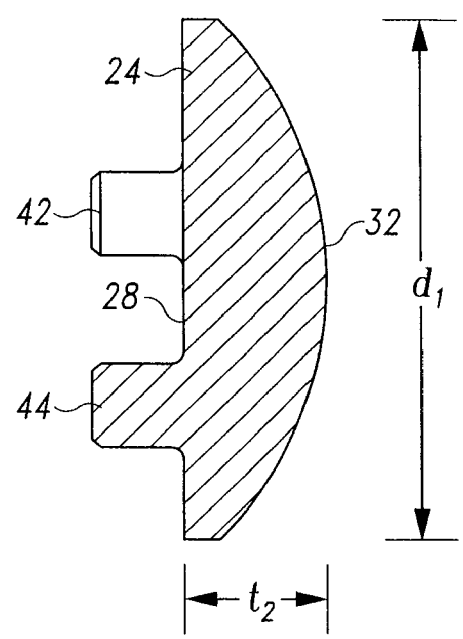
FIG. 9 is a cross-section of the patellar trial of FIG. 8, taken along line 9-9 of FIG. 8.
Figure 10:
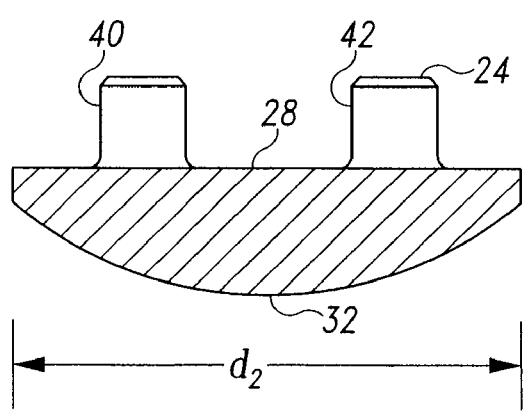
FIG. 10 is a cross-section of the patellar trial of FIG. 8, taken along line 10-10 of FIG. 8.

An example of a patellar implant is shown at 22 in FIGS. 5-7, and an example of a patellar trial is shown at 24 in FIGS. 8-10. In the illustrated embodiments, the patellar protector 10, implant 22 and trial 24 are generally oval in shape in plan view. However, it should be understood that the patellar protector, implant and trial could have other shapes, such as an overall circular shape, for example. The present invention is not limited to any particular shape of any of the components of the system or kit unless expressly called for in the claims.

Both the illustrated implant 22 and trial 24 have flat bone contacting surfaces 26, 28, opposite articulating surfaces 30, 32 and one or more mounting members 34, 36, 38, 40, 42, 44. The implant 22, trial 24 and patella protector 10 are intended to be separately mounted to a flat resected surface of the patella. The mounting members 16, 18, 20, 34, 36, 38, 40, 42, 44 of the implant, trial and patella protector are all similarly sized so that they may all be separately received in mating holes drilled into the resected patella. Thus, when mounted to the prepared patella, the mounting members 16, 18, 20, 34, 36, 38, 40, 42, 44 are received in holes in the patella and only the portions of the protector 10, implant 22 and trial 24 from the bone-contacting surfaces 14, 26, 28 to the bearing 12 and articulating surfaces 30, 32 extend beyond the resected surface of the patella.

As shown in FIGS. 6 and 9, the portions of the implant 22 and trial 24 that extend beyond the resected surface of the patella have maximum thicknesses shown at $t_1$ and $t_2$. Typically, the dimensions for $t_1$ and $t_2$ range from about 0.3 inches to about 0.45 inches. Generally, for each size of implant 22, the corresponding trial 24 would have the same thickness. In contrast, the patella protector 10 is much thinner, with a thickness shown at $t_3$ in FIG. 2 of about 0.04-0.08 inches (1-2 mm) Thus, when the patella protector 10 is mounted to the patella, a significant gap exists between the protector bearing surface 12 and the facing surface of the femur, a gap that decreases significantly when the protector 10 is removed and the implant 22 or trial 24 is mounted to the resected patella. The gap existing when the protector 10 is mounted to the patella is advantageous in improving the surgeon's ability to move the patella intraoperatively without unduly stressing the soft tissue connecting the patella to the femur and tibia, as described in more detail below.

The illustrated oval patella protector 10, implant 22 and trial 24 have overall lengths and widths, shown at $d_1$ and $d_2$, respectively, in FIGS. 2-3, 6-7 and 9-10. Typical dimensions for $d_1$ may range from about 1.26 inches to about 1.6 inches (32 mm-41 mm); typical dimensions for $d_2$ may range from about 1 inch to about 1.4 inches (25.4-40.6 mm) A typical system or kit would include several sizes of protectors 10, implants 22 and trials 24 to accommodate the size of the patient's patella.

It should be understood that the above shapes and dimensions are provided as examples only; the present invention is not limited to any particular shape or dimension unless expressly set forth in the claims.

The patella protector 10 can be made of a variety of materials. For example, surgical grade stainless steel could be used. Alternatively, a suitable plastic material could be used. Examples of suitable plastic materials are CELCON brand acetal copolymer and polysulphone. Alternatively, a combination of materials could be used for the patella protector; for example, the bearing surface 12 could be made of a thin sheet of metal mounted on a plastic base. Preferably, the material is resistant to fracture and can be sterilized. The patella protector 10 could be intended for single use or could be intended to part reusable; the choice of material can be expected to depend at least in part on the intended useful life of the patella protector 10. It may be desirable to make the patella protector out of a colored material so that the protector can be quickly and easily seen and distinguished from the patient's native tissue; for example, the patella protector could be black, green or red in color. It should be understood that the present invention is not limited to any particular material for the patella protector unless expressly called for in the claims.

The patellar implant 22 and patellar trial 24 can be standard commercially available products. Suitable implants and trials are available from DePuy Orthopaedics, Inc., of Warsaw, Ind. Commercially available implants 22 and trials 24 include products known as a three-peg oval dome patella, as shown in FIGS. 5-10. These implants 22 are typically made of ultrahigh molecular weight polyethylene. Patellar implants 22 and trials 24 are also available in a circular shape, and with a single mounting peg instead of the illustrated three mounting pegs. In addition, patellar implants are available that include an articulating surface made of a material having a low coefficient of friction mounted on a metal base; in such designs, the bone-contacting surface is on the metal base and the articulating surface is made of a material such as ultrahigh molecular weight polyethylene. It is expected that the present invention can be used with any type of patellar implant and trial.

Figure 21:
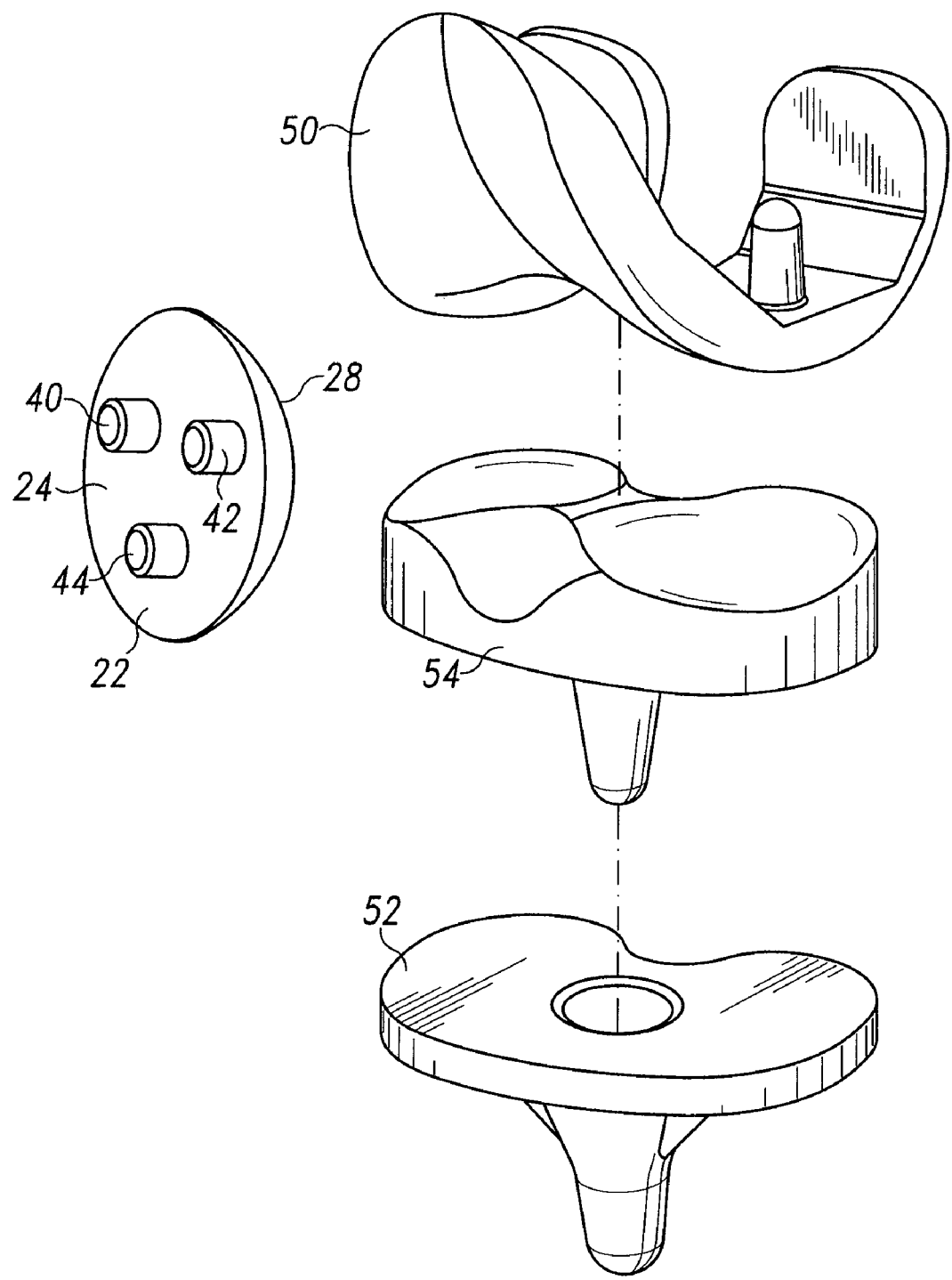
FIG. 21 is a perspective view of a femoral implant, patellar implant, tibial insert and tibial tray.

A typical surgical kit would also include other components to replace portions of the distal femur and proximal tibia. Such components are commercially available from DePuy Orthopaedics, Inc. of Warsaw, Ind. Suitable examples include prosthetic implant components of DePuy's P.F.C. Sigma Knee System, and other DePuy knee systems. Suitable trials and instrumentation for implanting these components are also available from DePuy Orthopaedics. FIG. 21 illustrates a prosthetic femoral implant 50, a prosthetic tibial tray 52, a tibial insert 54 and a patellar implant 22. Although the illustrated tibial component is a mobile bearing component, it should be understood that fixed bearing tibial components can be used as well.

It should be understood that these commercial products, materials and this supplier are provided as examples only. The principles of the present invention could be applied to the products of other manufacturers as well.

The above-described patella protector 10, trials 24 and implants 22 may be used in the surgical technique or method of the present invention. Using the components of the present invention, the surgeon can advantageously reduce the size of the incision made and can minimize soft tissue trauma.

Initially, a longitudinal incision is made from the superior pole of the patella and over the medial edge of the patella to a point about one centimeter proximal to the medial margin of the tibial tubercle. The incision may be extended if necessary to achieve exposure or to relax severe skin tension during the procedure.

The patella is the first bone resected in this method of performing TKR. The knee is fully extended, and the patella is turned and held vertically. The patella 60 is resected and a template is selected that covers the resected patellar surface without overhang. A peg hole or holes are then drilled into the patella. An appropriately sized patellar trial, such as trial 24, is placed on the resected patella, with the trial pegs 40, 42, 44 received in the peg holes in the patella. Overall patellar thickness is then assessed. Once the surgeon is satisfied with the patellar trial, the trial is removed and replaced with the patellar protector 10 of the present invention. The pegs 16, 18, 20 are placed in the peg holes and the bone-contacting surface 14 is placed against the resected surface of the patella. The diameter of the pegs 16, 18, 20 is similar to the diameter of the peg holes (and similar to the diameters of the pegs 34, 36, 38, 40, 42, 44 of the implant 22 and trial 24) so that position of the protector 10 is maintained without additional support. The patella may then be subluxated into the lateral gutter to expose portions of the distal femur and proximal tibia (see FIG. 12). Alternatively, the patella may be subluxated medially to expose portions of the distal femur and proximal tibia (see FIG. 13). With the patella subluxated, it is turned at an angle substantially less than a 180-degree eversion; instead, the patella is turned at an angle on the order of 90 degrees or less, substantially decreasing stress to the soft tissue associated with the patella.

Before subluxating the patella laterally, any osteophytes of the lateral femoral condyle should be removed. Since osteophytes of the lateral condyle can measure as much as 10 mm, it is desirable to remove such osteophytes to decrease soft tissue tension when the patella is subluxated along the lateral aspect of the lateral femoral condyle and moved into the lateral gutter. Similarly, if the patella is to be subluxated medially, osteophytes of the medial femoral condyle should be removed.

To expose the proximal tibia sufficiently for proper positioning of the cutting block, the proximal tibia is moved in the anteromedial direction toward the surgical opening. Simultaneously, the ligaments and tendons are protected to prevent undue stress during this movement of the proximal tibia. Movement of the tibia and tibial resection can be done with the knee in flexion.

Figure 11:
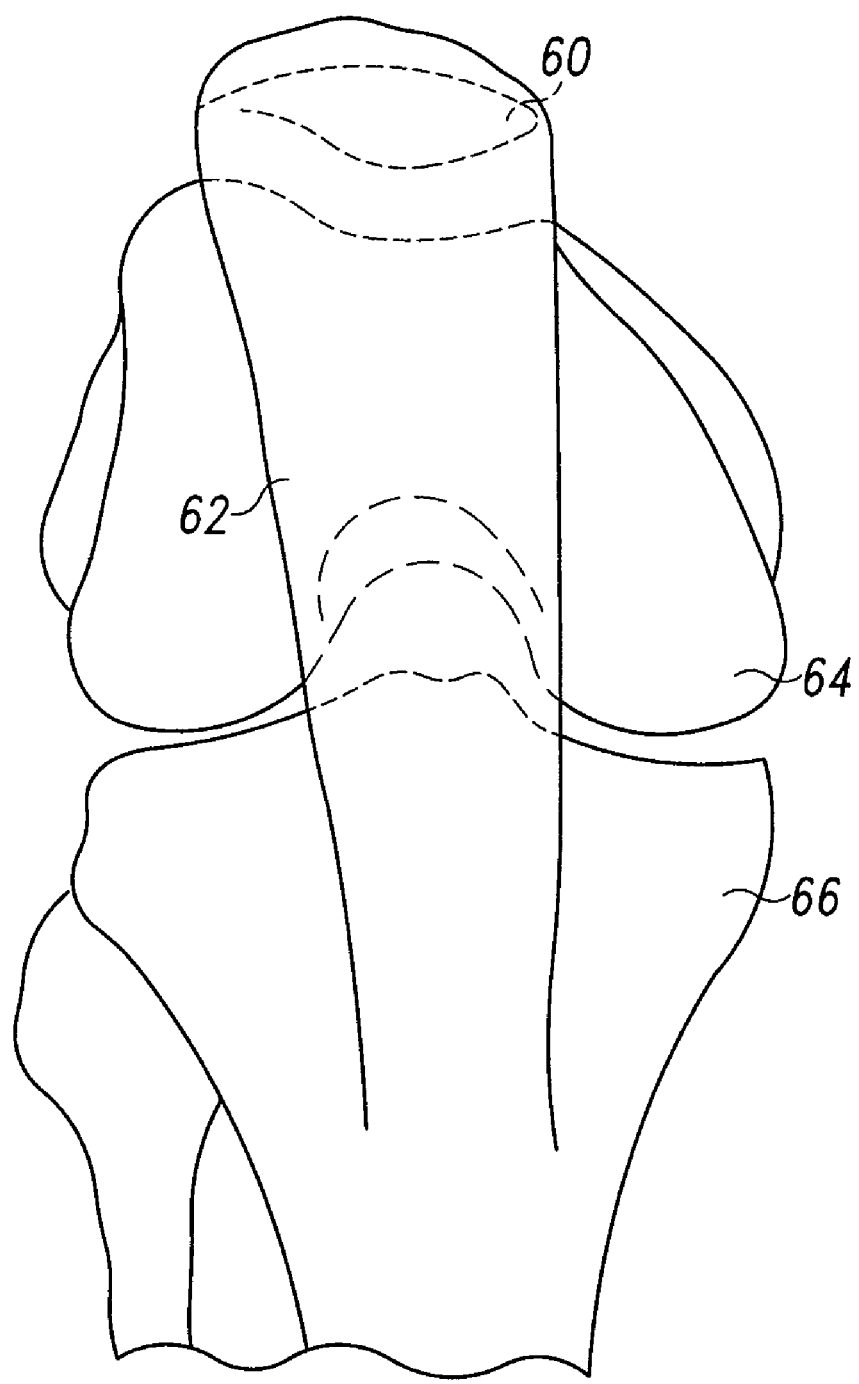
FIG. 11 is a diagrammatic representation of an anterior view of a knee in flexion.
Figure 12:
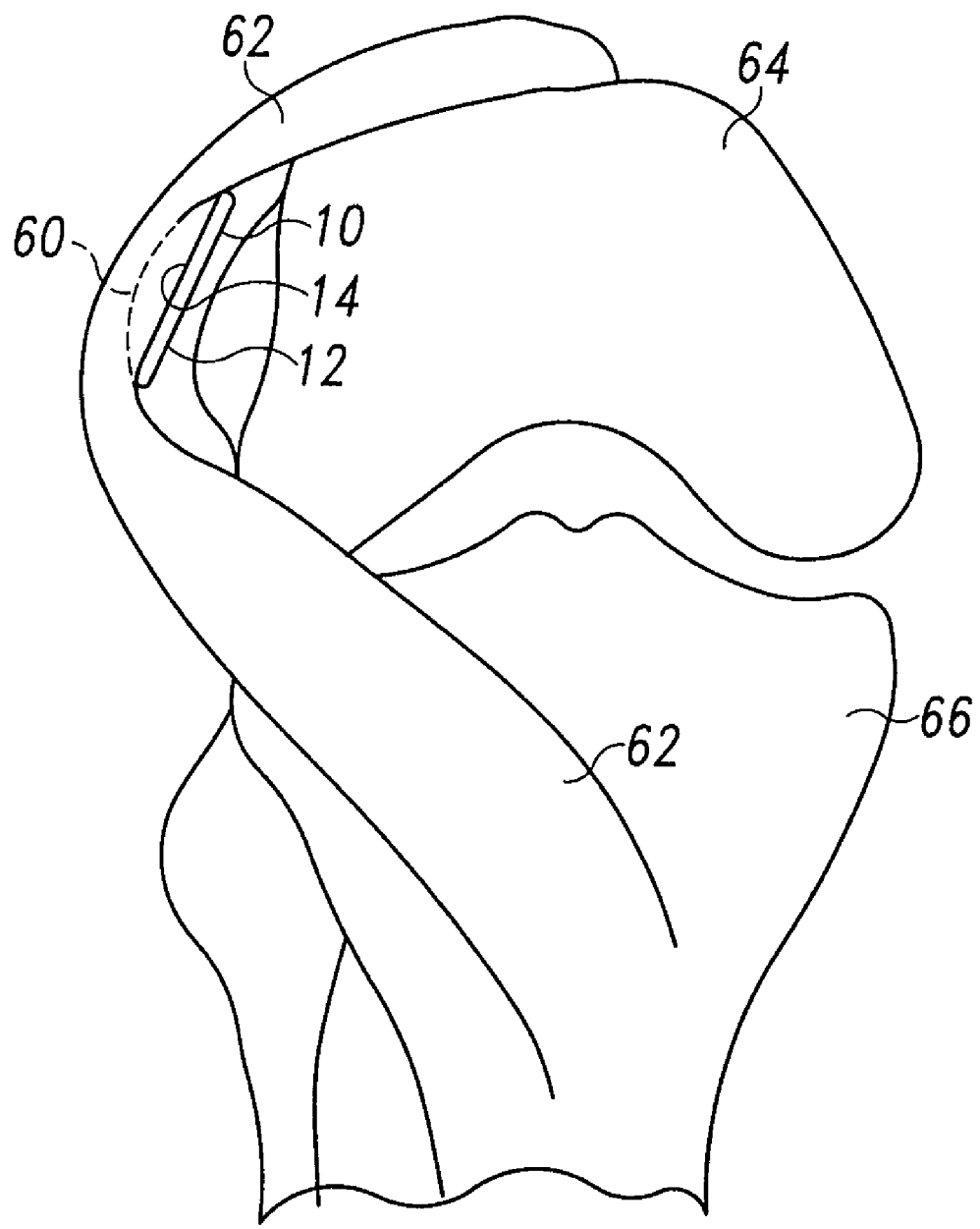
FIG. 12 is a diagrammatic representation of an anterior view of a knee in flexion with the patella resected, a patella protector mounted to the patella, and with the patella subluxated laterally.
Figure 13:
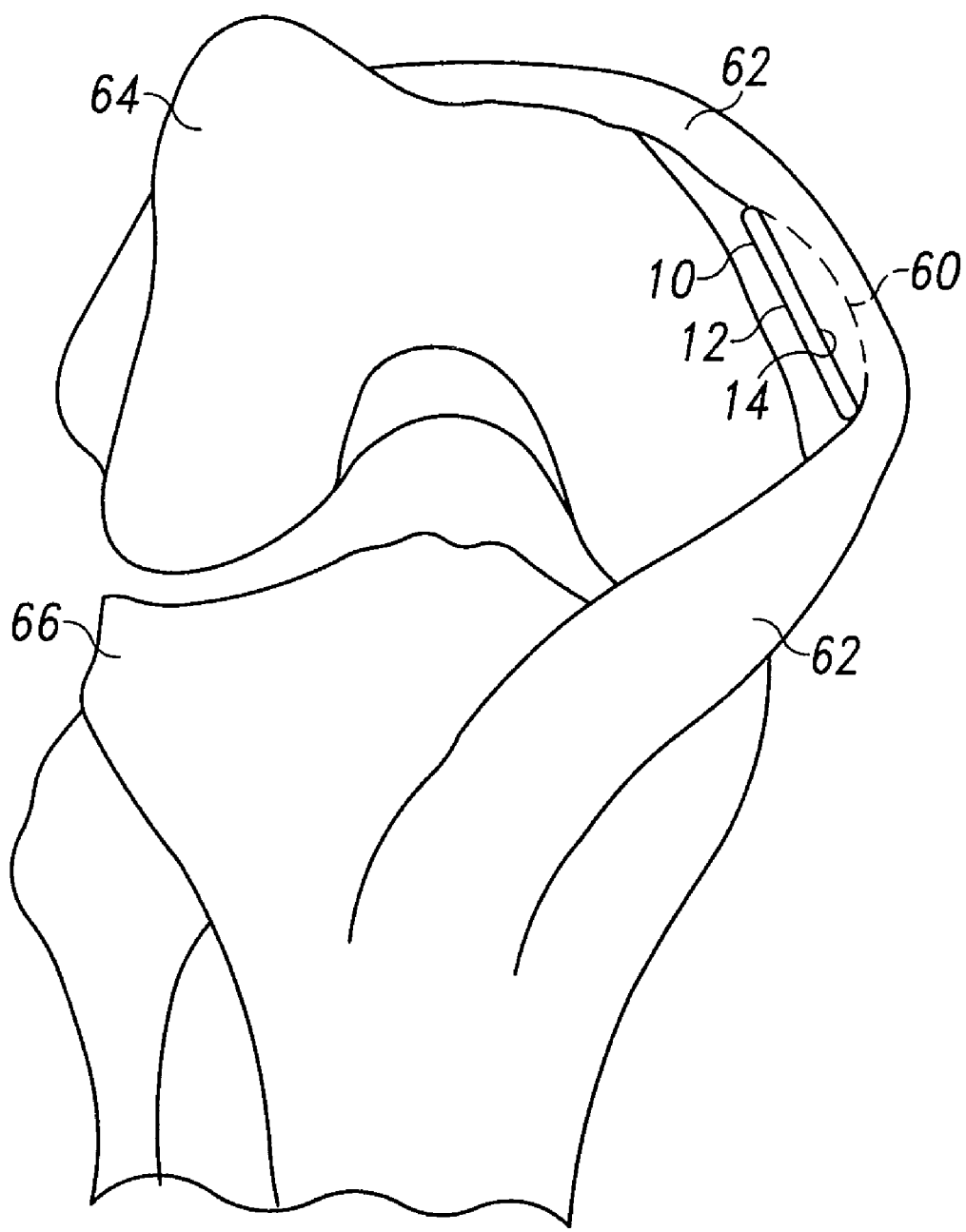
FIG. 13 is a diagrammatic representation similar to FIG. 12, but with the patella subluxated medially.
Figure 14:
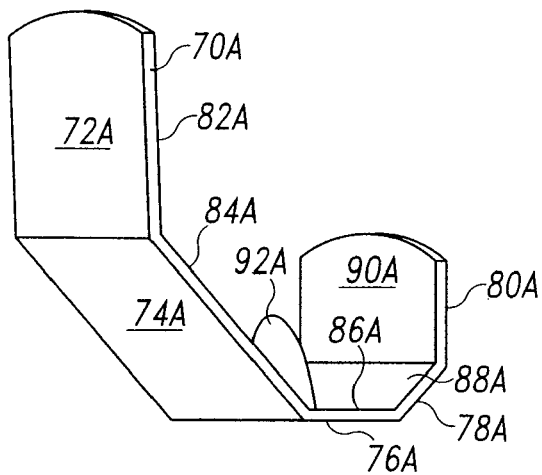
FIG. 14 is a perspective view of one embodiment of a femoral condyle protector.

FIGS. 11-13 illustrate a knee in flexion diagrammatically. FIG. 11 illustrates the native patella 60 and its associated soft tissue 62 and its relationship to the patient's distal femur 64 and proximal tibia 66. FIGS. 12 and 13 illustrate the patella 60 after it has been resected and after a patella protector 10 has been mounted to the resected surface of the patella. FIG. 12 also illustrates a position (lateral) of the subluxated patella 60 that can be used in the method of the present invention. FIG. 13 illustrates the resected patella and patella protector subluxated medially.

To move the proximal tibia in the anteromedial direction, force can be applied to the tibia from the posterolateral direction while protecting the patella and soft tissues from injury. To accomplish this combination of movement and protection, a 90-degree Hohman retractor and a straight Hohman retractor are used. Part of the 90-degree Hohman retractor may be placed against the lateral proximal tibia and part of the 90-degree retractor is placed against the bearing surface 12 of the patella protector 10. The end of the straight Hohman retractor is placed next to the posterior cruciate ligament on the proximal tibia. The surgeon then subluxates the tibia anteromedially, excising the anterior cruciate ligament and the roots of the posterior medial and lateral meniscus. The 90-degree Hohman retractor acts as a lever in this procedure, pivoting on the bearing surface 12 of the patella protector 10. After sufficient parts of the proximal tibia are exposed, the surgeon can then follow standard procedures in positioning a cutting block and resecting the tibial plateau.

More details of the surgical technique are provided in "P.F.C. Sigma Knee System with Specialist mini Instruments", to be published in 2004 by DePuy Orthopaedics, Inc. of Warsaw, Ind., publication no. 0612-57-500. A copy of this surgical technique is attached to and made a part of this patent specification and/or incorporated by reference herein in its entirety. Additional details may be found in the three-page document labeled "Disclosure", which is attached hereto and made a part of this patent specification and/or incorporated by reference herein in its entirety.

It will be appreciated that with the surgical technique of the present invention, the TKR procedure can be less invasive. A smaller initial incision may be made, and the potential for trauma to the soft tissue associated with the patella is substantially reduced.

Figure 15:
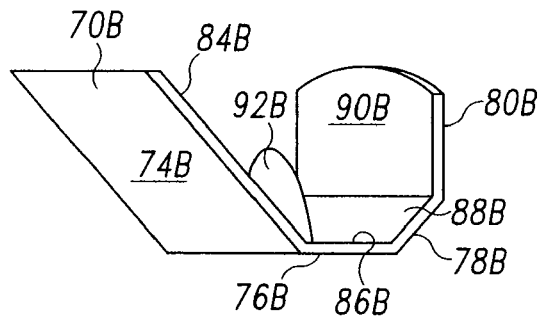
FIG. 15 is perspective view of another embodiment of a femoral condyle protector.
Figure 16:
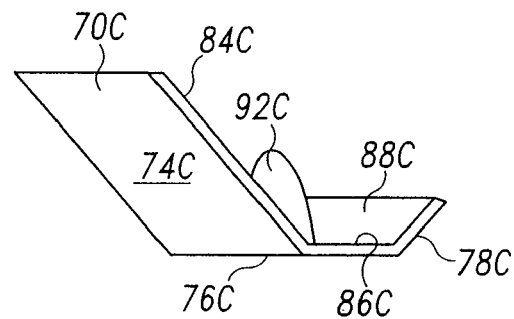
FIG. 16 is a perspective view of a third embodiment of a femoral condyle protector.
Figure 17:
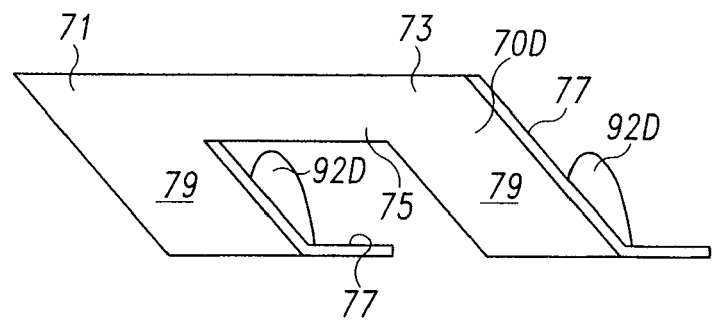
FIG. 17 is a perspective view of a fourth embodiment of a femoral condyle protector.

It will be appreciated by those skilled in the art that the principles of the present invention can be applied to the protection of other bones of the knee joint, and to the bones of other joints of the body as well. For example, it may be desirable to provide a tibial protector or a femoral condyle protector. FIGS. 14-17 illustrates various embodiments of femoral condyle protectors 70A, 70B, 70C, 70D. The first illustrated femoral condyle protector 70A includes a plurality of flat bearing surfaces 72A, 74A, 76A, 78A, 80A, a plurality of flat bone-contacting surfaces 82A, 84A, 86A, 88A, 90A and a mounting member 92A. The illustrated mounting member 92A corresponds in size, shape and position with one mounting peg of a corresponding femoral trial and femoral implant. The first illustrated femoral protector 70A is sized and shaped to cover the entire resected surface of a single femoral condyle, to facilitate use of the protector 70A in a minimally invasive procedure. Alternative shapes are possible. For example, as shown in FIGS. 15-16, a femoral condyle protector 70B, 70C could have fewer bearing surfaces 74B, 76B, 78B, 80B, 74C, 76C, 78C and bone-contacting surfaces 84B, 86B, 88B, 90B, 84C, 86C, 88C so that less than all of the resected distal femoral condyle is covered by a protector. It should be understood that other shapes are possible. In addition, two femoral protectors 70A, 70B, 70C of any of the types illustrated in FIG. 14-16 could be used. Instead of protecting only a single condyle, a femoral protector could cover all or some of the resected surfaces of both condyles of the distal femur. For example, as shown in FIG. 17, a femoral protector 70D could have two condylar portions 71, 73 joined by a bridge portion 75, all having both a plurality of bone-contacting surfaces 77 and a plurality of bearing surfaces 79. One or two mounting members 92D could also be provided. The femoral protector 70A, 70B, 70C, 70D can be made of the same material as the patella protector 10, and can be made to be thin, on the order of 1-2 mm. Although the resected distal femur would not be expected to have the inferior mechanical properties of the resected patella, any of the illustrated femoral protectors 70A, 70B, 70C, 70D could be useful in preventing damage (such as chipping or scratching) to the resected surfaces of the femur.

Figure 18:
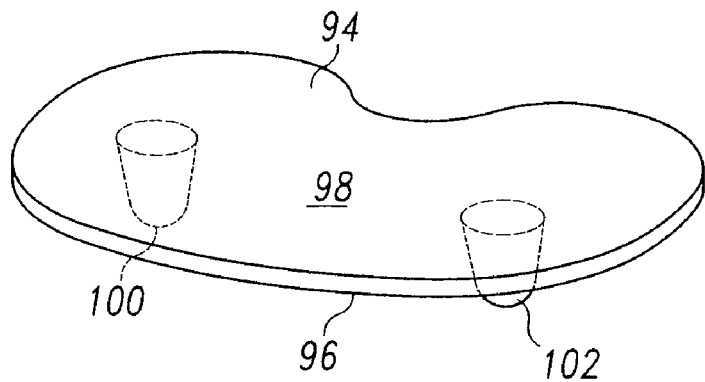
FIG. 18 is a perspective view of a tibial plateau protector.
Figure 19:
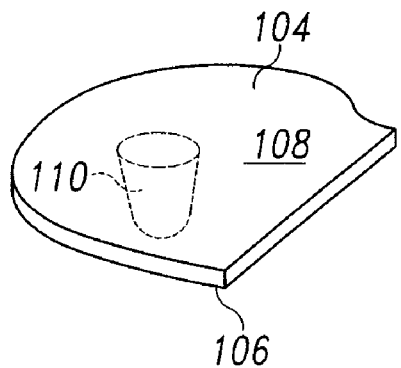
FIG. 19 is a perspective view of a medial tibial plateau protector.
Figure 20:
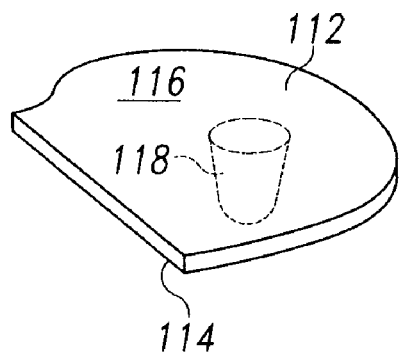
FIG. 20 is a perspective view of a lateral tibial plateau protector.

Similarly, the resected tibial plateau would not be expected to have the inferior mechanical properties of the resected patella. However, it may be desirable to provide a tibial protector 94 as illustrated in FIG. 18, or a two-piece tibial protector as shown in FIGS. 19-20. The one-piece tibial protector 94 of FIG. 18 has a bone-contacting surface 96, a bearing surface 98 and a pair of mounting members 100, 102. The two-piece protector comprises a medial tibial protector 104, with a bone-contacting surface 106, a bearing surface 108 and a mounting member 110, and a complementary lateral tibial protector 112, with a bone-contacting surface 114, a bearing surface 116 and a mounting member 118. The illustrated bearing surfaces 98, 108, 116 are flat, and the thickness of each protector 96, 104, 112 is on the order of 1-2 mm. It should be understood that the shapes of the tibial protectors 96, 104, 112 are provided as examples only; other shapes may be provided, depending for example, on whether the procedure is a cruciate sacrificing procedure. The illustrated tibial protectors can be made of the same materials as described above for the patella protector.

Although the illustrated embodiments all relate to protection of resected surfaces of the bones of the knee joint, it should be appreciated that the principles of the present invention can be applied to other joints as well. For example, appropriately sized and shaped protectors could be provided for the hip joint, shoulder joint, ankle joint, and elbow joint. Accordingly, reference to a "bone protector" in the claims should be interpreted to encompass not only the illustrated patella protector 10, femoral protector 70, and tibial protectors 96, 104, 112, but also to encompass protectors designed to protect the bones of other joints.

While only specific embodiments of the invention have been shown, it is apparent that various alternatives and modifications can be made thereto. Moreover, those skilled in the art will also recognize that certain additions can be made to the illustrated embodiment. It is, therefore, the intention in the appended claims to cover all such alternatives, modifications and additions as may fall within the true scope of the invention.

I claim:

1. A method of performing total knee arthroplasty comprising:
   obtaining a protector and a patella implant, the protector and the patella implant each having bone-contacting surfaces and exposed opposite surfaces, the exposed opposite surfaces of the protector and the patella implant having different shapes, the bone-contacting surface and the exposed opposite surface of the protector being flat, planar and substantially parallel to each other;
   resecting a portion of the patella to define a posterior plane extending over a majority of the proximal-distal dimension of the patella;
   covering at least a majority of the planar resected portion of the patella with the protector with the bone-contacting surface of the protector positioned against the planar resected portion of the patella;
   positioning an external implement against the exposed opposite surface of the protector and applying force to the external implement to move one of the bones of the knee;

resecting a portion of the distal femur and proximal tibia after the patella has been resected and moved and while the patella is covered with the protector;

removing the protector from the patella after the distal femur and proximal tibia have been resected; and affixing the patella implant to the resected patella after the distal femur and the proximal tibia have been resected and after the protector has been removed from the patella.

2. The method of claim 1 wherein the step of positioning an implement against the exposed opposite surface of the protector and applying force to move one of the bones comprises positioning a retractor on the exposed opposite surface of the protector on the covered resected portion of the patella and applying force to the retractor to move the proximal tibia.

3. The method of claim 2 wherein the distal femur and proximal tibia are resected without everting the patella.

4. The method of claim 2 wherein the proximal tibia is pushed in the anteromedial direction prior to resecting the proximal tibia.

5. The method of claim 1 wherein the distal femur and proximal tibia are resected without everting the patella.

6. The method of claim 1 further comprising subluxating the patella prior to resection of the femur and tibia.

\* \* \* \* \*